United States Patent
Wagner et al.

(10) Patent No.: US 7,718,441 B2
(45) Date of Patent: May 18, 2010

(54) AGENT AND METHOD FOR IDENTIFYING FURFURALS

(75) Inventors: Berthold Wagner, Frankfurt am Main (DE); Stefanie Beil-Seidler, Moerfelden-Walldorf (DE)

(73) Assignee: Merck Patent GmbH, Darmstadt (DE)

( * ) Notice: Subject to any disclaimer, the term of this patent is extended or adjusted under 35 U.S.C. 154(b) by 384 days.

(21) Appl. No.: 11/577,272

(22) PCT Filed: Sep. 16, 2005

(86) PCT No.: PCT/EP2005/009984

§ 371 (c)(1), (2), (4) Date: Apr. 13, 2007

(87) PCT Pub. No.: WO2006/042600

PCT Pub. Date: Apr. 27, 2006

(65) Prior Publication Data

US 2007/0287183 A1     Dec. 13, 2007

(30) Foreign Application Priority Data

Oct. 15, 2004    (DE) ........................ 10 2004 050 209

(51) Int. Cl.
*G01N 33/02* (2006.01)
*G01N 33/00* (2006.01)

(52) U.S. Cl. ............................ 436/169; 436/20; 436/93
(58) Field of Classification Search ................ 436/169, 436/20, 93
See application file for complete search history.

(56) References Cited

U.S. PATENT DOCUMENTS

| 3,992,158 | A | * | 11/1976 | Przybylowicz et al. ........ 422/57 |
| 5,296,192 | A | * | 3/1994 | Carroll et al. ................. 422/56 |
| 5,370,990 | A | | 12/1994 | Staniford et al. | |

FOREIGN PATENT DOCUMENTS

| DE | 270 847 A7 | 8/1989 |
| EP | 0 469 445 A1 | 2/1992 |
| EP | 0 526 150 A1 | 2/1993 |
| GB | 1 593 735 A | 7/1981 |
| GB | 1593735 * | 7/1981 |

* cited by examiner

*Primary Examiner*—Jill Warden
*Assistant Examiner*—Dwan A Gerido
(74) *Attorney, Agent, or Firm*—Mullen, White, Zelano, Branigan, P.C.

(57) ABSTRACT

The present invention relates to a composition and a method for the determination of furfurals, in particular the chemical signal substances 5-(hydroxymethyl)furan-2-carbaldehyde (hydroxymethylfurfural, HMF) and furan-2-carbaldehyde (furfural). The determination according to the invention is based on a liquid- or dry-chemical test using barbituric acid derivatives and 4-aminophenazone derivatives.

4 Claims, No Drawings

AGENT AND METHOD FOR IDENTIFYING FURFURALS

The invention relates to a composition and a method for the determination of furfurals, in particular the chemical signal substances 5-(hydroxymethyl)-furan-2-carbaldehyde (hydroxymethylfurfural, HMF) and furan-2-carbaldehyde (furfural).

Heat treatment is the commonest way of preserving foods and making them edible. Under precisely controlled conditions, the foods retain their inherent, organoleptic and nutrition-physiological properties under the heat treatment. Any heat treatment going beyond the requisite extent can modify the food constituents and thus adversely affect the taste and nutritional value together. Chemical signal substances are therefore frequently employed in order to assess the quality of foods and in order to control and optimise processes in food processing.

Hydroxymethylfurfural (HMF) is a known indicator of the loss of quality due to excessive heat treatment or storage of sugar-containing foods. The HMF content of fresh, untreated fruit juices is virtually zero, and the determination of the HMF content is a common method for assessing the effectiveness of a heat treatment for deactivation of undesired microorganisms in jams and fruit preparations.

HMF is a principal product of the Maillard reaction and is formed in the reaction of reducing sugars with amino acids, depending on the temperature and pH. In investigations of various foods, concentrations of greater than 1 g/kg of HMF have been found in dried fruit, caramel products and juices prepared from prunes.

The International Federation of Fruit Juice Processors (IF-FJP) recommends a maximum concentration of 5-10 mg/l of HMF in fruit juices and 25 mg/kg in fruit-juice concentrates.

In tomato juices and tomato purée, 1.3 to 186 mg/kg of HMF has been found, depending on the sugar and solids content (Brix value).

In fresh honeys, HMF can be determined in contents of less than 1 mg/kg, and honey having a content of 15 mg/kg or more is only suitable for use as industrial honey.

The HMF content also has some importance in milk processing, in particular ultra heat treatment. However, the varying HMF contents in the raw milk must be noted here.

Besides its importance as heating parameter in foods, the HMF content has a direct influence on the odour and taste of the foods which cannot be neglected.

The determination of the HMF content of foods and raw materials in food processing has become part of routine analysis in quality-control laboratories. Various methods are used, all of which require sample preparation, such as distillation or extraction. These include gas chromatography, HPLC or spectrophotometric determinations using the Winkler method (Winkler, 1955, Z. Lebensm.-Untersuch.-Forsch., 102, 161), or by the A.O.A.C. method.

All these methods require complex equipment as well as trained personnel for reliable performance.

In addition, these methods are not suitable for rapid on-site analysis, which would ensure control of the processing processes close to the analysis in terms of time.

The most frequently used method for HMF determination by the Winkler method (recommended in E.U. and O.I.V. guidelines) uses toxic p-toluidine (CAS No. 106-49-0), which, besides the health risk to the inexperienced user and the disposal problems of the residual substances produced, also excludes use in the spatial vicinity of food processing. In addition, the Winkler method hides the problem that the coloration formed is only stable for a short time and thus makes evaluation more difficult.

Replacement of the Winkler method for the determination of HMF and the provision of a user-friendly and inexpensive rapid test for HMF analysis, in particular in foods, are of high importance.

The invention therefore had the object of providing a composition for the determination of HMF which can be used directly on site without complex equipment.

It has been found that a reagent combination of a 4-aminophenazone derivative, in particular 4-aminophenazone (4-aminoantipyrine, CAS No. 83-07-8), and a barbituric acid derivative, in particular barbituric acid (CAS No. 67-52-7) or thiobarbituric acid (CAS No. 504-17-6), in acidic medium gives a red-violet coloration in the presence of HMF. This coloration can be evaluated visually or photometrically. In particular, the reagent combination can also be in the form of a test strip, enabling the HMF determination to be carried out particularly simply.

It has furthermore been found that the determination of other furfurals, such as, for example, 5-substituted furfural derivatives and furfural itself, is also possible using the same reagent combination. In addition, a distinction can be made between HMF and furfural, since a blue coloration occurs on use of 4-aminobenzoic acid in the presence of furfural, while HMF, by contrast, does not cause any coloration.

The present invention therefore relates to a composition for the determination of furfurals, at least comprising a barbituric acid derivative and a 4-aminophenazone derivative in acidic medium. An acidic medium is, in particular, an acidic aqueous solvent or a support to which an acidic impregnation solution has been applied.

In a preferred embodiment, the composition is in the form of a test strip.

In another preferred embodiment, the 4-aminophenazone derivative present in the composition is 4-aminophenazone.

In a further preferred embodiment, the barbituric acid derivative present in the composition is barbituric acid and/or thiobarbituric acid.

In a further preferred embodiment, the composition comprises citric acid.

In a particularly preferred embodiment, the composition consists of a test strip which has been impregnated with an acidic solution which comprises at least 0.1 to 20% by weight of 4-aminophenazone and 0.05 to 5% by weight of barbituric acid and/or thiobarbituric acid.

In another embodiment, the composition consists of a test strip which additionally has a zone which has been impregnated with an acidic solution which comprises at least 4-aminobenzoic acid and a barbituric acid derivative.

The present invention also relates to a method for the determination of furfurals, characterised by the following steps a) provision of an aqueous sample solution
b) bringing the composition according to the invention into contact with the sample solution from step a)
c) visual and/or photometric evaluation of the coloration formed.

In a preferred embodiment, a test strip according to the invention is employed in step b).

In a further preferred embodiment, the evaluation in step c) is carried out reflectometrically.

The present invention also relates to the use of the composition according to the invention for the determination of 5-(hydroxymethyl)furan-2-carbaldehyde in foods.

The present invention also relates to a kit for the determination of furfurals, at least containing a composition according to the invention in the form of a test strip.

In an embodiment, the kit additionally contains a test strip which has been impregnated with an acidic solution which comprises at least 4-aminobenzoic acid and a barbituric acid derivative.

The crux of the present invention is that a combination of a barbituric acid derivative and a 4-aminophenazone derivative gives rise to an intense, generally red to violet-blue coloration in acidic solution in the presence of furfurals, in particular 5-(hydroxymethyl)furan-2-carbaldehyde and/or furan-2-carbaldehyde. In the presence of 5-(hydroxymethyl)furan-2-carbaldehyde, a rather more red-violet coloration is formed, while a rather more blue-violet coloration is formed in the presence of furan-2-carbaldehyde. The colour can vary depending on the type of barbituric acid derivatives and 4-aminophenazone derivatives employed.

A sample solution is any type of aqueous or at least predominantly aqueous solution. It can be an undiluted sample, such as, for example, in the case of juices or other beverages, such as beer or wine. However, the sample may equally firstly be diluted or dissolved with water or a buffer solution. This is necessary, for example, in the case of highly concentrated or viscous or non-liquid samples, such as, for example, jams or honey.

In the case of samples which are not directly miscible with water, an extraction can first be carried out. This is necessary, for example, for the determination of 5-(hydroxymethyl)furan-2-carbaldehyde and/or furan-2-carbaldehyde in oils. The person skilled in the art is able to carry out one or more extraction steps with water and/or water-miscible solvents and/or aqueous buffer solutions.

In any case, it is advantageous for the sample solution ultimately employed for the determination to be an aqueous, clear and not excessively coloured solution. It has furthermore been found that the presence of sulfite interferes with the determination according to the invention.

In the case of very strongly basic or strongly, in particular basically, buffered sample solutions, acidification may be necessary before the determination according to the invention is carried out, since the colour reaction according to the invention only occurs in acidic medium. In general, however, it is sufficient to bring the samples into contact with the composition according to the invention without prior acidification.

For the purposes of the present invention, 4-aminophenazone derivatives are 4-aminophenazone and derivatives of this compound which carry another substitution, preferably a $C_2$- to $C_5$-alkyl radical, instead of the methyl group in the 1- and/or 5-position. The phenyl ring may equally be mono- or polysubstituted, for example by $C_1$- to $C_5$-alkyl radicals. In a preferred embodiment, the 4-aminophenazone derivative employed is 4-aminophenazone itself.

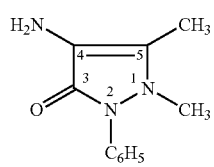

Formula I shows by way of example the 4-aminophenazone which is preferred in accordance with the invention.

Barbituric acid derivatives are barbituric acid and thiobarbituric acid themselves, and derivatives which carry, independently of one another, $C_1$- to $C_6$-alkyl and/or $C_6$- to $C_{18}$-aryl radicals, such as, for example, methyl, ethyl, isopropyl, cyclohexyl or phenyl, on one or both ring nitrogen atoms. An example of a barbituric acid derivative of this type is 1,3-dimethylbarbituric acid.

In a preferred embodiment, barbituric acid and/or thiobarbituric acid are used in accordance with the invention.

In accordance with the invention, the terms "4-aminophenazone derivative" and "barbituric acid derivative" mean that in each case individual compounds or a mixture of such compounds are used.

The composition according to the invention is preferably in the form of a reagent solution or particularly preferably in the form of a test strip.

A reagent solution according to the invention typically comprises at least 0.1 to 20% (% by weight), preferably 3 to 8%, in particular about 5%, of the 4-aminophenazone derivative and 0.05 to 5% (% by weight), preferably about 0.2%, of the barbituric acid derivative in an acidic aqueous solvent. The aqueous solvent can be water or an aqueous buffer system, which may comprise up to 75% (% by vol.) of a water-miscible solvent, such as, for example, ethanol. In a preferred embodiment, the solvent consists of equal parts by volume of ethanol and an acidic aqueous solution. In a particularly preferred embodiment, the pH of the solvent is between 2 and 5, particularly preferably about 3.5. In order to set this pH, inorganic or organic acids and bases are suitable. For example, it is possible to prepare an aqueous solution from 50 g/l of citric acid in water, whose pH is adjusted to pH 3.5 using sodium hydroxide solution.

In a particularly preferred embodiment, the composition according to the invention is in the form of a test strip. Analysis using solid, sorptive supports, so-called test strips, has increasingly gained importance in recent years. The essential advantages of this dry-chemical method include, in particular, simple handling and straightforward disposal due to the small amounts of reagent. All or the majority of the reagents necessary for the determination reaction (colouring reagent, buffer system, optionally also stabilisers and solubilisers) are embedded in corresponding layers of a solid, sorptive or swellable support to which the sample is applied. After contact of the reaction zone with the sample, the determination reaction proceeds. The colour formed is a measure of the amount of analyte to be determined and can be evaluated visually, i.e. semi-quantitatively by comparison with a colour chart, or quantitatively, for example using simple reflectometers.

Sorptive supports which can be used are all materials which are usually in use for such tests. The most widespread is the use of filter paper, but it is also possible to employ other sorptive cellulose, glass-fibre or plastic products. The reagents may also be embedded in transparent support layers whose film-forming components are swellable in water. The film-forming components may be of natural origin, such as, for example, gelatine, agarose, alginate, or of synthetic origin, such as, for example, cellulose esters, polyvinyl acetate, polyethyleneimine, polyvinyl alcohol. The sorptive supports are impregnated in a known manner with impregnation solutions which comprise the reagents necessary for the determination. The impregnated and dried supports, preferably papers, can either be cut into manageable strips as such or they can be converted into preferably square zones, which may themselves be bonded to or sealed onto or into plastic films, paper strips or metal strips in a known manner.

The impregnation solution for the composition according to the invention in the form of a test strip typically comprises at least 0.1 to 20%, preferably 3 to 8%, in particular about 5%, of a 4-aminophenazone derivative and 0.05 to 5%, preferably about 2%, of a barbituric acid derivative in an acidic aqueous solvent. The aqueous solvent can be water or an aqueous buffer system, which may comprise up to 75% (% by vol.) of a water-miscible solvent, such as, for example, ethanol. In a preferred embodiment, the solvent consists of equal parts by volume of ethanol and an acidic aqueous solution. In a particularly preferred embodiment, the pH of the solvent is between 2 and 5, particularly preferably about 3.5. In order to set this pH, inorganic or organic acids and bases are suitable. For example, it is possible to prepare an aqueous solution from 50 g/l of citric acid in water, whose pH is adjusted to pH 3.5 using sodium hydroxide solution.

In the preferred embodiment, this impregnation solution is applied to a film band with sealed-on filter-paper zone and dried in a stream of warm air. After cutting into test strips, these are available for qualitative and also quantitative analyses.

The present invention also relates to a method for the determination of furfurals, in particular 5-(hydroxymethyl)furan-2-carbaldehyde and/or furan-2-carbaldehyde, characterised by the following method steps a) Provision of an Aqueous Sample Solution It may be necessary here firstly to convert the sample to be analyzed into a suitable form, for example by dilution, dissolution or extraction.

b) Bringing the Composition According to the Invention into Contact with the Sample Solution from Step a)

In the case of a composition according to the invention in the form of a reagent solution, this is added in suitable amount to the sample solution. Depending on the concentration of the analyte in the sample solution, mixing ratios between 1:10 and 10:1 are typical. The person skilled in the art can discover the suitable mixing ratio by means of a few experiments. In the case of test strips, these are wetted with the sample solution or dipped briefly into the sample solution. If necessary, the sample solution here can be correspondingly diluted or concentrated in advance. Depending on the analyte content in the sample solution, a colour development typically occurs within 1 to 10 minutes, with the colour development on a test strip usually taking place after only 1 to 3 minutes.

c) Visual and/or Photometric Evaluation of the Coloration Formed

The colour development can be evaluated by comparison with a colour chart and/or, preferably, by quantitative analysis using a reflectometer.

The composition and method according to the invention are particularly suitable for the determination of HMF and/or furfural in foods. The reagents preferably employed are non-toxic. In particular, the test strips preferably employed may also be employed directly on site by untrained personnel. For quantitative analysis, no further equipment is necessary apart from a small hand reflectometer. HMF concentrations between 0.3 and 100 mg/l can typically be determined using the composition and method according to the invention.

In contrast to the Winkler method, in which the colour development fades after only a few minutes, significantly better colour stability can be achieved with the compositions according to the invention. The reagent solutions according to the invention exhibit at least a colour stability over at least 15 to 30 minutes. The test strip according to the invention is particularly preferred since here the colour is typically already developed after 1 to 3 minutes and then remains stable for hours to days. The composition according to the invention is preferably therefore employed in the form of a test strip or in the form of a kit which contains at least one test strip according to the invention. In a preferred embodiment, the kit additionally contains a colour chart and solvents for dilution or extraction of the samples, depending on the type of samples.

It has furthermore been found that a composition according to the invention no longer exhibits a colour reaction in the presence of HMF on replacement of the 4-aminophenazone derivative by 4-aminobenzoic acid, whereas a blue colour occurs in the presence of furfural. In this way, a distinction can be made between HMF and furfural, enabling both HMF and furfural both to be determined semi-quantitatively and/or quantitatively in a single sample. To this end, the sample is analyzed using a composition according to the invention and the content of furfurals (typically only HMF and furfural) is thus determined. In addition, a further analysis is carried out using a composition in which the 4-aminophenazone derivative has been replaced by 4-aminobenzoic acid. The furfural content can thus be determined. The HMF content is then given by the difference between the two results.

The present invention therefore also relates to a method and composition for the parallel determination of HMF and furfural in a single sample.

In a preferred embodiment, the composition is a test strip which comprises a reagent combination of at least one 4-aminophenazone derivative and a barbituric acid derivative in acidic medium in one zone and a reagent combination which comprises at least 4-aminobenzoic acid and a barbituric acid derivative in acidic medium in another zone. In this way, the determination can be carried out in parallel on a single test strip.

The parallel determination of HMF and furfural can equally be carried out with the aid of a kit which contains at least a composition according to the invention which comprises at least one 4-aminophenazone derivative and a barbituric acid derivative in acidic medium and a composition which comprises at least 4-aminobenzoic acid and a barbituric acid derivative in acidic medium. These may be two reagent solutions or also two test strips.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding application DE 102004050209.9, filed on 15 Oct. 2004, is incorporated into this application by way of reference.

EXAMPLES

1. Compilation of a Calibration Line a) Preparation of Reagent Solution

5% (% by weight) of 4-aminophenazone and 0.2% (% by weight) of barbituric acid are dissolved in a solvent. The solvent consists of equal parts by volume of ethanol and a buffer solution consisting of 50 g/l of citric acid in water; the pH of the solvent is adjusted to 3.5 using sodium hydroxide solution. If an HMF solution in deionised water is added to the reagent solution in the volume ratio 10/1, the following absorbances (cell thickness 1 cm, 550 nm arise at 20° C. after a reaction time of 15 min:

TABLE 1

| HMF in mg/l | Absorbance |
|---|---|
| 0 | 0.006 |
| 5 | 0.081 |
| 10 | 0.157 |
| 20 | 0.315 |
| 50 | 0.795 |
| 100 | 1.536 |

These values give a straight line with the equation $y=0.0153x+0.0077$ and a correlation coefficient of 0.9998.

Real samples (both calibrated with HMF standards) were investigated comparatively using the Winkler method and the reagent solution according to the invention.

The following measurement values were obtained:

TABLE 2

| | Winkler method | | | Method according to the invention | | |
|---|---|---|---|---|---|---|
| | Absorbance | | | Absorbance | | |
| Sample | PIW | Sample | HMF (mg/l) | PIW | Sample | HMF (mg/l) |
| Grape juice a natural | 0.276 | 0.787 | 14 | 0.022 | 0.282 | 16 |
| Grape juice a doped with 20 mg/l of HMF | 0.243 | 1.414 | 35 | 0.022 | 0.560 | 34 |
| Grape juice b natural | 0.203 | 0.854 | 19 | 0.011 | 0.326 | 20 |
| Grape juice b doped with 20 mg/l of HMF | 0.179 | 1.469 | 39 | 0.011 | 0.618 | 38 |
| Apple juice a natural | 0.138 | 0.159 | 1 | 0.005 | 0.034 | 2 |
| Apple juice a doped with 20 mg/l of HMF | 0.129 | 0.812 | 21 | 0.005 | 0.334 | 21 |
| Apple juice b natural | 0.134 | 0.142 | 0 | 0.001 | 0.022 | 1 |
| Apple juice b doped with 20 mg/l of HMF | 0.132 | 0.823 | 21 | 0.001 | 0.330 | 21 |
| Honey 20 g dissolved in 80 g of water | 0.146 | 0.345 | 5 | 0.012 | 0.078 | 4 |
| Honey 20 g dissolved in 80 g of water doped with 20 mg/l of HMF | 0.129 | 0.897 | 23 | 0.012 | 0.396 | 24 |
| 20 mg of HMF in water | 0.133 | 0.819 | 20 | 0.003 | 0.319 | 20 |

PIW denotes blank value

2. Determination of HMF in Apple Juice

Reflectometric Evaluation of the Reaction Colour

Production of the Test Sticks:

The following impregnation solution is applied to a filter paper (for example Binzer, type 1588) and then dried using warm air.

The paper is sealed onto a white support film using hot-melt adhesive (for example Dynapol 1272) and cut suitably into strips, so that a reaction zone of about 6 mm×8 mm is formed.

Composition of the Impregnation Solution:
250 g of buffer solution (comprising 50 g of citric acid dissolved in 1000 g of deionised water and adjusted to pH 3.5 using NaOH)
250 g of ethanol
25.0 g of 4-aminophenazone
1.0 g of barbituric acid Analysis:

The test stick is dipped into the sample to be investigated or standard solution for about 2 seconds, shaken off briefly and evaluated in the reflectometer (RQflex®) after a reaction time of two minutes.

The correlation between the measured relative remission (%) and the HMF content is shown in Table 1.

TABLE 3

| HMF in mg/l | % rem |
|---|---|
| 0 | 81.4 |
| 5 | 71.5 |
| 10 | 63.5 |
| 20 | 52.4 |
| 50 | 36.8 |
| 100 | 25.0 |

3. Practical Tests

Practical Test 1:

Various food samples are investigated using the method according to the invention and compared with the Winkler photometric method.

Sample Preparation:
For pale juices: none.
For honeys: dissolve 10 g in 40 g of water in an ultrasound bath.

TABLE 4

| Sample | Photometric Winkler method | Method according to the invention with RQ-Flex ® evaluation |
|---|---|---|
| Standard solution 5 mg/l of HMF | 5.0 | 4.2 |
| Standard solution 20 mg/l of HMF | 21.1 | 18.1 |

TABLE 4-continued

| Sample | Photometric Winkler method | Method according to the invention with RQ-Flex ® evaluation |
|---|---|---|
| Grape juice white a. | 0.7 | 0.3 |
| Grape juice white b. | 2.1 | 2.1 |
| Apple juice a. | 1.4 | 1.6 |
| Apple juice b. | 0.4 | 0.3 |
| Apple juice c. | 2.4 | 3.0 |
| Wild honey | 0.3 | 0.3 |
| Acacia honey | 0.4 | 0.3 |
| Sunflower honey | 3.6 | 3.1 |

Doping experiments with 10 mg/l or 10 mg/kg of HMF show the following results:

The measurements by the two methods were carried out with the same sample (natural or doped).

TABLE 5

| Sample | Photometric Winkler method | | | Method according to the invention with RQ-Flex ® evaluation | | |
|---|---|---|---|---|---|---|
| | natural | doped | recov. | natural | doped | recov. |
| Water | 0 | 12.0 | 120% | 0 | 10.3 | 103% |
| White wine a. | 0.3 | 11.0 | 107% | 0.3 | 8.6 | 81% |
| White wine b. | 2.4 | 14.0 | 116% | 3.0 | 13.8 | 105% |
| White wine c. | 6.5 | 17.7 | 112% | 5.9 | 15.8 | 96% |
| Grape juice | 13.7 | 25.9 | 122% | 23.6 | 36.0 | 120% |
| Apple Juice | 1.7 | 13.5 | 118% | 2.1 | 13.4 | 110% |
| Sunflower honey | 3.0 | 14.5 | 115% | 5.0 | 18.3 | 129% | recov. means recovery

The invention claimed is:

1. A method for the determination of furfurals, comprising:
   a) a composition comprising a barbituric acid derivative and a 4-aminophenazone derivative in an acidic medium
   b) an aqueous sample solution
   c) bringing the barbituric acid and 4-aminophenazone composition into contact with the sample solution
   d) visual and/or photometric evaluation of the coloration formed, and determining the presence of fufurals.

2. The method according to claim 1, wherein a test strip is employed in step b).

3. The method according to claim 1, wherein the evaluation in step c) is carried out reflectometrically.

4. A method for the determination of 5-(hydroxymethyl) furan-2-carbaldehyde in foods, comprising visual or photometric evaluation of a solution of said food that has been contacted with a composition of claim 1 to determine the presence of said 5-(hydroxymethyl)furan-2-carbaldehyde.

* * * * *